United States Patent
Morrow et al.

[11] Patent Number: 5,891,622
[45] Date of Patent: Apr. 6, 1999

[54] ASSESSMENT OF OXIDATIVE STRESS IN VIVO

[75] Inventors: Jason D. Morrow, Nashville, Tenn.; Hyesook Kim, Bloomfield Hills, Mich.; L. Jackson Roberts, II, Nashville, Tenn.; Denis M. Callewaert, Oxford, Mich.

[73] Assignees: Oxford Biomedical Research, Inc., Oxford, Mich.; Vanderbilt University, Nashville, Tenn.

[21] Appl. No.: 28,543

[22] Filed: Feb. 24, 1998

Related U.S. Application Data

[60] Provisional application No. 60/038,496, Feb. 25, 1997.
[51] Int. Cl.⁶ .............................. C12Q 1/00; C12Q 1/26; C12Q 1/02
[52] U.S. Cl. .................................... 435/4; 435/29; 435/25
[58] Field of Search ..................................... 435/4, 29, 25

[56] References Cited

U.S. PATENT DOCUMENTS 5,700,654  12/1997  Roberts et al. ........................... 435/25

OTHER PUBLICATIONS

Awad et al: Hepatology, vol. 22(3), pp. 962–968, (1995) (Abstract).

*Primary Examiner*—Louise N. Leary
*Attorney, Agent, or Firm*—Kohn & Associates

[57] ABSTRACT

A method to assess oxidative stress in vivo by measuring the amount of free, esterified and glucuronidated forms of isoprostanes (8EPGF2) in a biological sample which contains the isoprostanes is disclosed. The method further includes determining the amount of total isoprostanes present in the sample. This amount is compared with a control sample. The oxidative stress is determined through the comparison wherein the amount of isoprostanes increase in the sample isolated from an organism undergoing oxidative stress compared to the control. Alternatively the method of the present invention provides for only the measurement of the glucuronidated form wherein the amount of glucuronidated isoprostanes increase in the sample isolated from an organism undergoing oxidative stress compared to the control.

10 Claims, 7 Drawing Sheets

ASSESSMENT OF OXIDATIVE STRESS IN VIVO

GOVERNMENT SUPPORT

Research in this application was supported in part by a grant from the National Institutes of Health (GM47634). The Government has certain rights in the invention.

CROSS REFERENCE TO RELATED APPLICATIONS

This application claims benefit under 35 USC §119(e) of United States Provisional Patent Application Ser. No. 60/038,496, filed Feb. 25, 1997.

BACKGROUND OF THE INVENTION

1. Field of the Invention

This invention relates to a method to analyze in vivo oxidative stress status in an organism by measuring glucuronidated forms of isoprostanes isolated from the organism and determining a total isoprostane profile including the glucuronidated form.

2. Description of Related Art

Oxidative stress, i.e. free radicals derived from oxygen, when occurring in vivo in biological systems, including cells and organisms, disrupts cellular structures and functions and contributes to disease development and aging. It would be useful to determine the oxidative stress level in vivo so as to provide a measure of the potential for disease development [Halliwell, et al 1987].

Isoprostanes are a novel class of prostaglandin-like compounds formed in vivo or in vitro by a non-cyclooxygenase-dependent free-radical catalyzed mechanism [Morrow, et al, 1990a]. In normal humans, levels of free (non-conjugated) form of 8-epi-prostaglandin $F_{2\alpha}$, (8EPGF2) measured by gas chromatograph and mass spectroscopy (GC/MS) provide a normal range from 5–50 pg/mL plasma and 500–3,000 pg/mg urinary creatinine, respectively [Morrow, et al, 1990a; 1990b; Morrow and Roberts, 1991]. The in vivo concentration of 8EPGF2 increases dramatically in animal models of lipid peroxidation [Awad, et al 1994], a model oxidative stress.

$F_2$-isoprostanes are formed from bicycloendoperoxide intermediates. Analogous to cyclooxygenase derived compounds the endoperoxide intermediate products of prostaglandin synthase (prostaglandin $G_2$ and prostaglandin $H_2$) are unstable and can also undergo non-enzymatic rearrangement to $PGD_2$ and $PGE_2$ (t½=~5 minutes in aqueous solution). Therefore, the possibility that the bicyclic endoperoxide precursors of 8EPGF2 undergo rearrangement to D-ring and E-ring isoprostanes was investigated and found that the $D_2/E_2$-isoprostanes are in fact formed in vivo in addition to $F_2$-isoprostanes [Morrow, et al 1994]. In contrast to 8EPGF2, free $D_2/E_2$-isoprostanes were not detectable (<5 pg/mL) in the circulatory system of untreated rats, but were found at significant levels in rats treated with $CCl_4$ to generate free radical induced lipid peroxidation [Morrow, et al 1994].

Therefore, measurement of isoprostane concentrations correlate with free radical production and this measurement has significant diagnostic potential for assessment of oxidative stress and disorders such as hepatorenal syndrome [Awad, et al, 1994], atherosclerosis [Morrow, et al, 1995], and carcinogenesis [Takahashi, et al, 1992]. High concentration of serum 8EPGF2 was found, in part, to be responsible for the kidney failure due to the intense vasoconstriction of renal arteries in hepatorenal syndrome patients [Awad, et al, 1994]. Free isoprostanes have been measured in plasma and urine as a relative measure of oxidative stress in vivo.

However, in any assay for isoprostanes all forms of the isoprostanes need to be considered and their metabolites may need to be considered. Assays for the free form are known. However, there is a concern about measurements of only the free (non-conjugated) form being completely representative. A significant portion [Morrow et al, 1997] of the free form in urine is probably derived locally from the kidney and does not represent systemic oxidant stress. For other body fluids isoprostanes may also be esterified to phospholipid [Morrow et al, 1997], and both free and esterified increase in oxidant stress. Therefore it is apparent that measurement of only the free form may provide an incomplete picture of oxidant stress in vivo.

8EPGF2 has a vasoconstrictor property [Morrow and Roberts, 1991; Morrow, et al, 1994], which may be, in part, mediated by binding to the thromboxane receptor [Fukunaga, 1993] or a distinct 8EPGF2 receptor [Rich and Singh, 1979]. Thus, any structural change of 8EPGF2 due to esterification or conjugation will be expected to affect binding of the 8EPGF2 to the receptors.

Free isoprostanes have been measured by mass spectrometry [Morrow, et al, 1990a; 1990b; Morrow and Roberts, 1991; Awad, et al, 1994]. This method is not well suited for routine clinical determinations due to:

(a) sample preparation for GC/MS is long and tedious, (b) this method assesses only free isoprostanes, and (c) it is not practical to measure all the possible 8EPGF2 metabolites using GC/MS. Recently, free 8EPGF2 in serum and urine specimens were measured using an ELISA. However this assay again does not provide a complete picture of oxidative stress since the assay does not measure all forms and metabolites of the isoprostanes which is necessary to provide a complete profile or better representation of oxidative stress in vivo.

SUMMARY OF THE INVENTION

According to the present invention, a method to assess oxidative stress in vivo by measuring the amount of free, esterified and glucuronidated forms of isoprostanes (8EPGF2) in a biological sample which contains the isoprostanes is disclosed. The method further includes determining the amount of total isoprostanes present in the sample. This amount is compared with a control sample(s). The oxidative stress is determined through the comparison wherein the amount of isoprostanes increase in the sample isolated from an organism undergoing oxidative stress compared to the control.

The present invention also provides a method to assess oxidative stress in vivo by measuring the amount of glucuronidated isoprostanes in a biological sample containing the isoprostanes and comparing the measured amount with a control sample and thereby assessing the oxidative stress through said comparison wherein the total amount of glucuronidated isoprostanes increases in the sample compared to the control.

Recent data obtained by the inventors, which measured total 8EPGF2 levels using ELISA, showed that (a) there are other forms of isoprostanes including esterified forms which are recognized by a polyclonal antibody produced against 8EPGF2 used in the Examples herein, and (b) one of the forms of 8EPGF2 in the biological system is a glucuronidated form and is not recognized by the antibody. The levels of the glucuronidated form can be measured by ELISA after enzymatic hydrolysis of the glucuronidated molecules. Therefore, the method of the present invention to measure total 8EPGF2 levels including free, esterified and glucuronidated isoprostanes, and such metabolites of isoprostanes has been developed to more fully assess the oxidant status of an individual.

DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

According to the present invention, a method to assess oxidative stress in vivo by measuring the amount of free, esterified and more particularly the glucuronidated forms of isoprostanes (8EPGF2) in a biological sample which contains the isoprostanes is disclosed. The method further includes determining the amount of total isoprostanes present in the sample. This amount is compared with a healthy control sample(s). In general a panel of healthy control samples is used that are within the normal range. The normal range is established as known in the art and is established for each assay method being utilized, e.g GC/MS and immunoassays. The oxidative stress is determined through the comparison wherein the amount of isoprostanes is increased in the sample isolated from an organism undergoing oxidative stress compared to controls.

Figure 7:
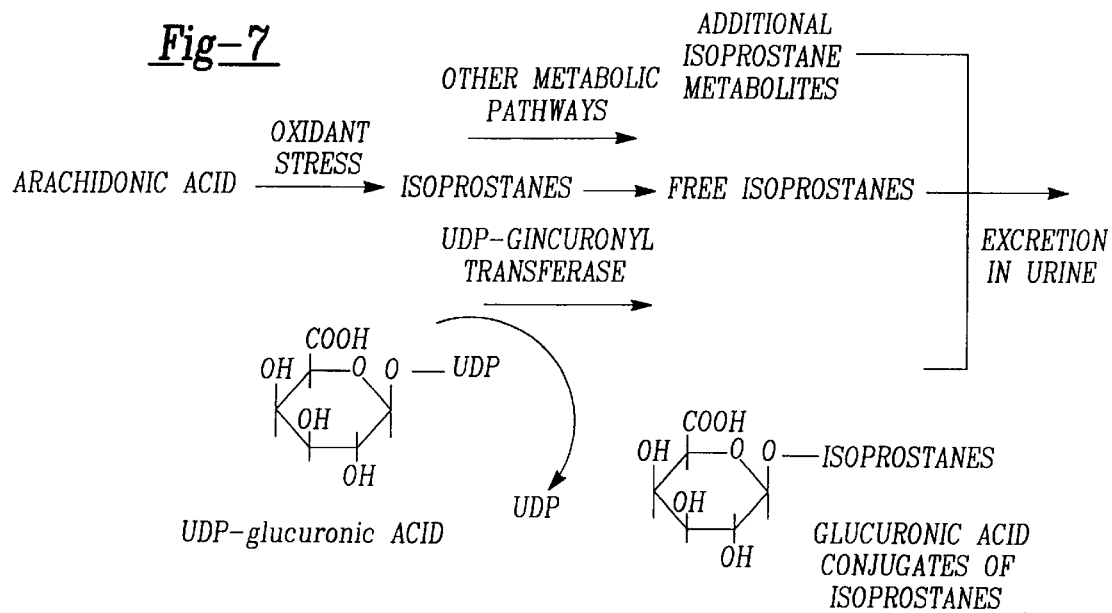
FIG. 7 is a schematic diagram of the production of glucuronidated isoprostanes.

It has been previously shown that oxidative stress is reflected in free isoprostane levels as discussed herein above. Applicants determined the presence of esterified (Example 2) and glucuronidated (Examples 2 and 3) forms of the isoprostanes and have determined that a total profile or amount of all forms of the isoprostanes (see FIG. 7) provides a fuller picture and assessment of oxidative stress.

Further, a measurement of the glucuronidated form itself provides an strong reflection of the oxidative stress status in the organism. In a preferred embodiment the profile utilizes the amount of glucuronidated isoprostanes as a reflection of oxidative stress. Given that UDP-glucuronyl-transferase is expressed primarily in the liver [Jansen et al, 1991], measurement of isoprostane glucuronides should reflect systemic production of isoprostanes that are glucuronidated to facilitate excretion. Therefore a large percentage of the free isoprostanes produced in various tissues are conjugated to glucuronic acid in the liver and are therefore a better indicator of oxidative stress. In contrast, a large proportion of the free form excreted in urine is produced in the kidney [Morrow et al, 1997] and so does not as accurately reflect a stress response in the entire organism.

It was unexpected to find a glucuronidated form of the isoprostanes as this form has not previously been disclosed or suggested [Roberts, 1987] and glucuronidated forms of the closely related prostaglandins have not been identified. Glutathione conjugates have been suggested [Rosenkranz et al, 1980a; 1980b] but were not characterized.

The biological sample is generally selected from biological fluids which contain lipids or lipid metabolites and can include plasma, urine, cerebrospinal fluid, bile and joint fluid. Urine is the preferred sample.

In general the quantification of the sample is done utilizing an immunoassay as described in the Examples herein. However alternative immunoassays or GC/MS can be used. Most of the techniques used in performing immunoassays are widely practiced in the art, and most practitioners are familiar with the standard resource materials which describe specific conditions and procedures. However, for convenience, the following paragraph may serve as a guideline.

In general, ELISAs are the preferred immunoassays employed to assess the amount of isoprostanes in a specimen. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,,879,219; 5,011,771 and 5,281,521 and may be adapted to be used in the method of the present invention.

The free and esterified forms of the isoprostanes are measured utilizing the immunoassay as set forth for example in the Examples herein with an antibody which recognized both forms. Alternatively, antibodies can be utilized which are specific for each form. Such antibodies can be produced as described herein below and tested as set forth in Example 1.

In one embodiment to measure the amount of glucuronidated isoprostanes, the glucuronidated form is separated from the free and done esterified forms. This can be done utilizing a column system as described herein in the Examples. This provides a free fraction and a glucuronidated fraction. The glucuronidated fraction is then hydrolyzed to release free isoprostanes. The released free form isoprostanes are then quantified as a means of determining the amount of glucuronidated isoprostane from which they were derived.

Alternatively, rather than separate the fractions, an aliquot of the sample is measured for the free/esterified forms of the isoprostanes in an immunoassay with an antibody which recognizes the free/esterified form. An aliquot of the sample is then hydrolyzed and the amount of isoprostanes measured which provides a measure of the total isoprostanes in the system including the free, esterified and glucuronidated. By subtraction the amount of glucuronidated form is thereby determined and a profile of oxidative stress in the organism determined. The profile that is determined can therefore reflect the total isoprostane complement, the free complement, the esterified complement or glucuronidated complement.

The amount of glucuronidated isoprostane present in the sample can be measured directly utilizing for example an immunoassay. In this embodiment the immunoassay utilizes an antibody specific for the glucuronidated form. Most of the techniques used to produce antibodies are widely practiced in the art, and most practitioners are familiar with the standard resource materials which describe specific conditions and procedures. However, for convenience, the following paragraphs may serve as a guideline.

Antibody Production: Antibodies (immunoglobulins) may be either monoclonal or polyclonal and are raised against the immunogen, the glucuronidated isoprostane. Conveniently, the antibodies may be prepared against the immunogen or part of the immunogen. Such immunogens can be used to produce antibodies by standard antibody production technology well known to those skilled in the art as described generally in Harlow and Lane, *Antibodies: A Laboratory Manual*, Cold Spring Harbor Laboratory, Cold Spring Harbor, N.Y., 1988 and Borrebaeck, *Antibody Engineering—A Practical Guide*, W. H. Freeman and Co., 1992. Antibody fragments may also be prepared from the antibodies and include Fab, F(ab')$_2$, and Fv by methods known to those skilled in the art.

For producing polyclonal antibodies a host, such as a rabbit or goat, is immunized with the immunogen, generally together with an adjuvant and, if necessary, coupled to a carrier; antibodies to the immunogen are collected from the sera. Further, the polyclonal antibody can be absorbed such that it is monospecific. That is, the sera can be absorbed against related immunogens, e.g. the free and esterified forms of isoprostanes, so that no cross-reactive antibodies remain in the sera thereby rendering it monospecific. Testing for this specificity can be undertaken as described in Example 1.

For producing monoclonal antibodies the technique involves hyperimmunization of an appropriate donor with the immunogen or immunogen fragment, generally a mouse, and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

For producing recombinant antibody (see generally Huston et al, 1991; Johnson and Bird, 1991; Mernaugh and Mernaugh, 1995), messenger RNAs from antibody producing B-lymphocytes of animals, or hybridoma are reverse-transcribed to obtain complimentary DNAs (cDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody.

The antibody or antibody fragment can be bound to a solid support substrate or conjugated with a detectable moiety or be both bound and conjugated as is well known in the art to be used in the immunoassay. (For a general discussion of conjugation of fluorescent or enzymatic moieties see Johnstone & Thorpe, *Immunochemistry in Practice*, Blackwell Scientific Publications, Oxford, 1982.) The binding of antibodies to a solid support substrate is also well known in the art. (see for a general discussion Harlow & Lane *Antibodies: A Laboratory Manual*, Cold Spring Harbor Laboratory Publications, New York, 1988 and Borrebaeck, *Antibody Engineering—A Practical Guide*, W. H. Freeman and Co., 1992) The detectable moieties contemplated with the present invention can include, but are not limited to, fluorescent, metallic, enzymatic and radioactive markers such as biotin, gold, ferritin, alkaline phosphatase, β-galactosidase, peroxidase, urease, fluorescein, rhodamine, tritium, $^{14}$C and iodination as needed for the immunoassay.

The above discussion provides a factual basis for the method of the present invention to measure total 8EPGF2 levels including free, esterified and conjugated glucuronidated isoprostanes, and metabolites of isoprostanes as a profile of oxidative stress of an individual. The methods used with and the utility of the present invention can be shown by the following non-limiting examples and accompanying figures.

EXAMPLES
MATERIALS AND METHODS
Materials

8EPGF2 (<98% pure by HPLC and GC/MS) was kindly provided by Dr. Gordon Bundy, Upjohn Corporation, and [$^3$H]-labeled 8EPGF2 (Specific activity, 23.4 Ci/μmol) was obtained from SibTech Inc. (Tenafly, N.J.). [$^2$H$_4$]-PGF$_{2\alpha}$ was obtained from Cayman Chemical Co. (Ann Arbor, Mich.). Horseradish peroxidase-conjugated donkey anti-goat Immunoglobulin G (IgG) was purchased from Jackson ImmunoResearch Laboratories, Inc. (West Grove, Pa.). The 9α,11β-PGF$_{2\alpha}$, 13,14-dihydro 15-keto-PGF$_{2\alpha}$, 13,14-dihydro 15-keto-PGF$_{2\alpha}$, 9β, 11a-PGF$_{2\alpha}$, 6-keto-PGF$_{1\alpha}$, PGE$_2$, PGD$_2$, and arachidonic acid were obtained from Biomol Research Lab. (Plymouth Meeting, Pa.). A colorimetric substrate for horseradish peroxidase, 3,3',5,5,'tetramethylbenzidine (TMB) with hydrogen peroxide, was obtained from ELISA Technologies (Lexington, Ky.). Low-density lipoprotein (LDL), oxidized LDL, and high-density lipoprotein (HDL) were obtained from Perlmmune, Inc. (Rockville, Md.). A lipase from the yeast, *Candida cylindraccae*, was obtained from Sigma Chemical Co. (St. Louis, Mo.). Reacti-gel used to cross-link anti-8EPGF2 IgG was purchased from Pierce (Rockford, Ill.). Sephadex G-25M PD-10 gel filtration columns were obtained from Pharmacia Co. (Piscataway, N.J.). Other reagents were purchased from Sigma Chemical Co.

Antibody Production

Synthetic 8EPGF2 was coupled to bovine serum albumin (BSA) using dicyclohexylcarbodiimide as previously described [Levine and VanVunakis, 1972; Pace-Asciak and Wolfe, 1971; see also herein above]. The conjugate was used to immunize a goat and antibody titers were determined by ELISA using 8EPGF2 conjugated to ovalbumin.

Purification of Immunoclobulin G (IgG) Fraction of Antisera

IgG fractions of antibody prepared against 8EPGF2 was purified from sera using protein-G affinity chromatography (Pierce Co.). The IgG bound to the protein G column was eluted with 50 mM glycine-HCl buffer, pH 2.5, and immediately neutralized with 0.5M Tris-HCl, pH 7.6. The procedure did not affect the specificity of the antibodies.

Immunoaffinity Column Chromatography

Figure 1:
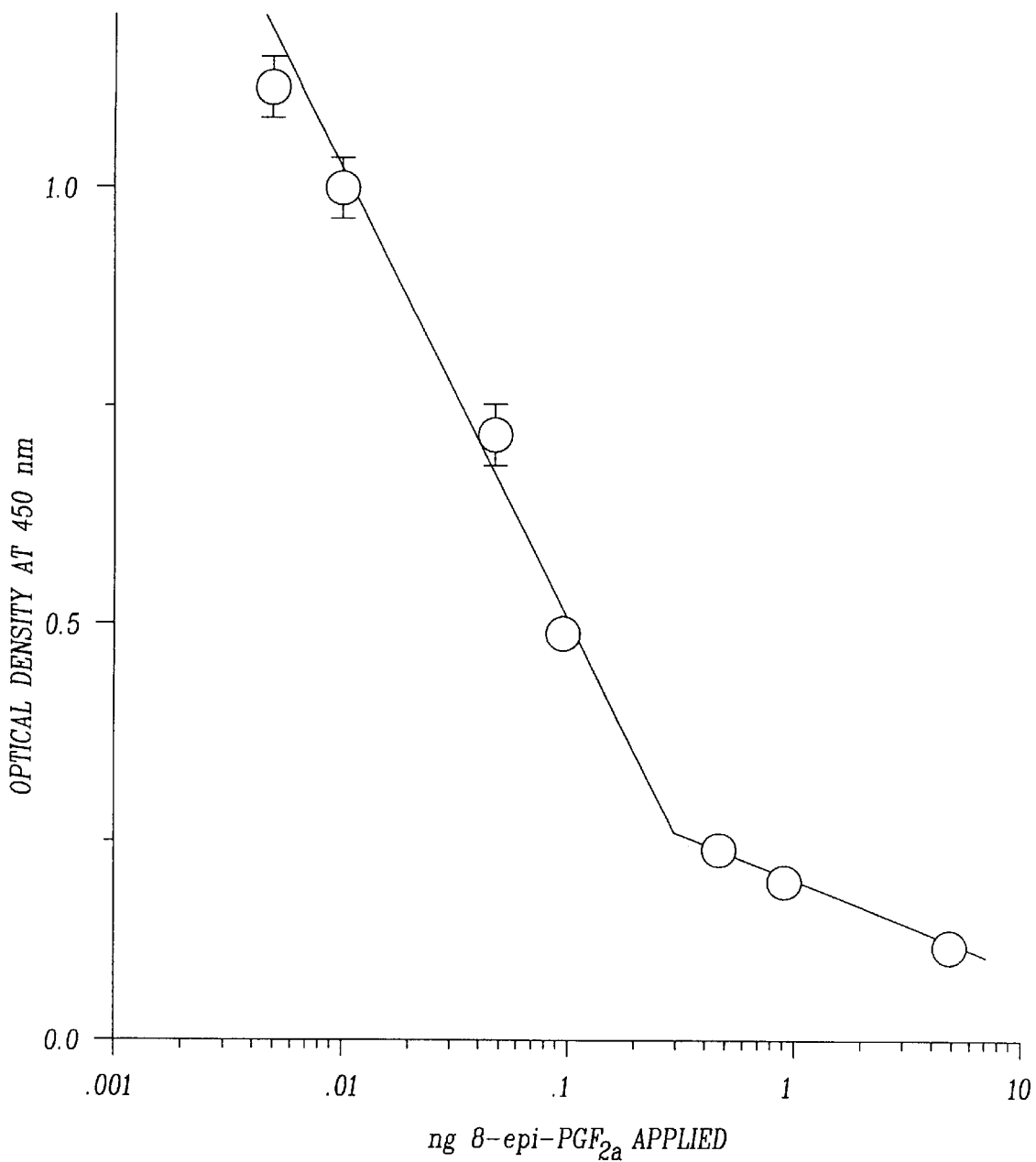
FIG. 1 is a graph showing retention of 8-epi-prostaglandin $F_{2\alpha}$ (8EPGF2) in an immunoaffinity column.

Reacti-gel was obtained from Pierce Co. and anti-8EPGF2 immunoaffinity column was prepared according to the manufacturer's instruction. Capacity of the immunoaffinity column was measured by applying increasing amounts of 8EPGF2 (FIG. 1). Bound 8EPGF2 was washed with phosphate-buffered saline (PBS), pH7.4, twice and eluted with acetonitrile:water (1:3), followed acetone:water (90:10) and quantitated by ELISA. In each experiment samples were diluted to concentrations lower than the capacity of the column (~0.5 ng/100 $\mu$L) prior to application to the column.

Solid Phase Competitive Enzyme-Linked Immunosorbent Assay (ELISA)

High-binding strip well microplates (Labsystems, Inc., Marlboro, Ma.) were coated with protein G-purified IgG suspended in 1M carbonate, pH 9.0, (1 $\mu$g/well; 200 $\mu$L/well final volume) and then covered with parafilm. After overnight incubation at room temperature, the wells were gently washed five times with tris buffered saline (TBS), pH 7.5, containing 0.1% tween. Non-specific sites were blocked by the addition of 0.2 mL of 5% (w/v) nonfat dry milk in TBS. After 2 hours of incubation at room temperature, the plates were washed three times with TBS-tween. One $\mu$g/well of purified IgG was sufficient for quantitation of 10 to 1000 pg/well of 8EPGF2. Samples and standards (150 $\mu$L) were added and the plates were preincubated for 20 minutes and 15 ng of the 8EPGF2-horseradish peroxidase (HRP) conjugated in TBS was added. Following incubation for 1 hour to permit competitive binding to bound antibody, unbound material was removed by thoroughly washing the wells with TBS-tween and 150 $\mu$L of a calorimetric substrate for HRP [3,3',5,5'tetramethylbenzidine (TMB) with hydrogen peroxide] (ELISA Technologies) was added. After incubation of the plate for 20 minutes, the reaction is stopped by addition of 75 $\mu$L of 1N $H_2SO_4$, and the absorbance at 450 nm determined using a microtiter plate reader. Under these assay conditions, the amount of color in a well is inversely proportional to the initial concentration of the sample or standard ligand. After subtraction of blank, the mean maximum absorbance reading ($B_O$) in the absence of unconjugated 8EPGF2 under these assay conditions ranged from 1.7 to 1.85.

Sample preparation for Gas Chromatography/Negative Ion Chemical Ionization-Mass Spectroscopy (GC/NICI-MS) (Two Column Method)

The 8EPGF2 levels in urine specimens were quantitated using GC/NICI-MS following pretreatment of specimens as previously described [Awad, et al, 1993]. Briefly, samples were acidified to pH 3.0 and applied to C18 column for solid phase extraction in which the column is first washed with 10% acetonitrile in water, pH 3.0, followed by washing with n-heptane, and the sample was eluted with ethyl acetate-:heptane (1:1). The eluate was applied to silica solid phase extraction in which the loaded column is washed with ethyl acetate and the isoprostanes eluted with ethyl acetate:methanol (1:1).

GC/MS of 8EPGF2

Compounds were dissolved in acetonitrile and GC/NICI-MS was carried out as described previously [Awad, et al, 1993; Lynch, et al, 1994]. Electron ionization mass spectra were obtained on a Finnigan Incos 50B quadruple instrument interfaced to a Hewlett-Packard 5890 gas chromatography. GC was carried out using 15 m, 0.25-mm diameter, 0.25-$\mu$m film thickness, DB1701 fused silica capillary column (J&W Scientific, Folsom, Calif.). The column temperature was from 190 to 300° C. at 2° C./minute. Methane was used as the carrier gas at a flow rate of 1 mL/minute. Ion source temperature was 250° C., electron energy was 70 eV, and filament current was 0.25 mA. Compounds were analyzed as pentafluorobenzyl ester, trimethylsilyl ether derivatives monitoring peaks in m/z 569 ion current chromatograms. The 8EPGF2 peak was identified by comparison of elution time of the peak with that of an internal standard, [$^2H_4$]PGF$_{2\alpha}$ (m/z=573), as previously described [Morrow, et al, 1990b; 1995].

Lipoprotein treatment

LDL, oxidized LDL, and HDL in 0.15M NaCl, 0.001% EDTA solution, pH 7.2, were digested with a lipase obtained from yeast, Candida cylindraccae, at 37° C. for 1 to 2 hours (1 mg of lipase/100 $\mu$g of lipoprotein). Lipids were extracted with methanol:chloroform (2:1) solution [Proudfoot et al, 1995]. The extracted lipids were kept in a silicated glass tube and sonicated for 5 minutes before each experiment. For in vitro oxidation experiment, antioxidants and low molecular weight contaminants in LDL were removed by passing through Sephanex G-25M PD-10 gel filtration columns (Pharmacia Co.) according to manufacturer's instructions prior to incubation of LDL (100 mg/ml) with 5 $\mu$M $CuSO_4$ at 37° C. for 0–4 hours. Ailquots were removed at intervals and spun in microtubes. Supernatants were removed and digested with the yeast lipase for 2 hours before quantitation of 8EPGF2 levels by ELISA. Minor oxidation of LDL observed during lipase digestion was subtracted from final 8EPGF2 levels.

Hydrolysis of glucuronidated 8EPGF2

$\beta$-Glucuronidase was dissolved 75 mM phosphate buffer, pH, 6.8, 170 $\mu$g of the dissolved $\beta$-glucuronidase solution was added to 1 mL urine specimen or to 1 mL solution of immunoaffinity column purified fraction. The sample was incubated at 37° C. for 2 hours.

Measurements of 8EPGF2 levels in urine specimens of tobacco smokers and non-smokers Clinical protocols for collection of urine samples and pair-matching for smokers with non-smokers were carried out as previously described [Morrow et al, 1995]. Levels of 8EPGF2 in urine samples was measured by ELISA (six separate measurements, 3 repetitions for each experiment) and normalized to creatinine levels obtained using an assay kit (Sigma Co.).

Statistics

Statistical analysis were performed using Statview 512™ (Brain Power, Inc., Calabasas, Calif.). Significance between groups was analyzed using one factor anova (Fisher PLSD).

EXAMPLE 1

DEVELOPMENT OF THE IMMUNOASSAY

Sensitivity of IgG Produced against 8EPGF2

Figure 2A:
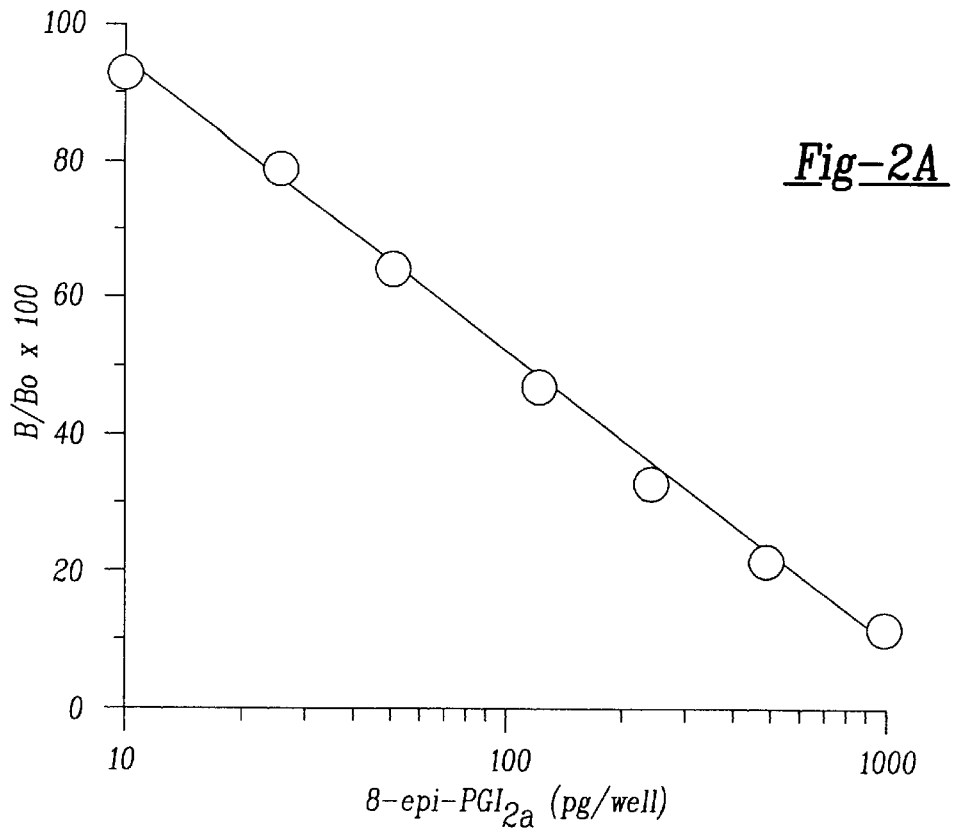
FIGS. 2A–B are graphs showing the sensitivity of IgG produced against 8-epi-prostaglandin F2α (8EPGF2): (A) is a typical standard curve for 8EPGF2 in a competitive ELISA and (B) levels of 8EPGF2 in urine after serial dilution.
Figure 2B:
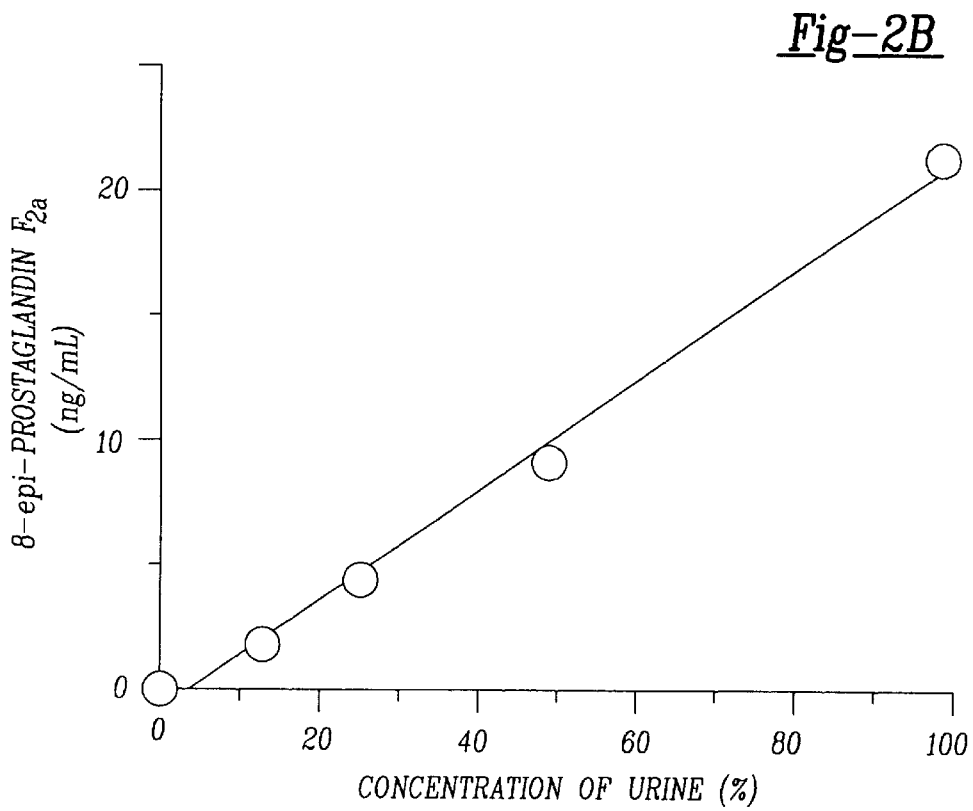

Titers of anti-8EPGF2 IgG obtained following immunization of goat with 8EPGF2 conjugated to BSA were determined by ELISA using 8EPGF2 conjugated to ovalbumin. Using this technique, the 3rd, 4th and 5th bleeds produced antibody titers greater than 1:16,000. Non-specific binding to plates coated with ovalbumin was negligible. A typical standard curve for 8EPGF2 is presented in FIG. 2A. For this experiment the $r^2$ value for the fit of the data to an equation describing an inverse logarithmic relationship of free 8EPGF2 to B/Bo was 0.998. For several independent runs, $r^2$ values ranged from 0.995–0.999. Levels of 8EPGF2 in urine samples were determined by ELISA after serial dilution. The levels of 8EPGF2 proportionally decreased following 2-, 4-, and 8-fold dilutions of the urine sample (FIG. 2B).

Specificity of anti-8EPGF2 IgG among Eicosanoids

Figure 3:
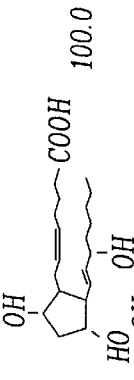
FIG. 3 is a listing of the panel of eicosanoids used to analyze the specificity of the 8EPGF2 ELISA. These eicosanoids were selected based on the similarity of their structure to 8EPGF2, as being anticipated to potentially compete with 8EPGF2 for binding to anti-8EPGF2 and thus interfere with such assays.

The specificity of the 8EPGF2 ELISA was investigated using authentic 8EPGF2 and a panel of eicosanoids (FIG. 3) which, based on their structure, might be anticipated to compete with 8EPGF2 for binding to anti-8EPGF2 and thus interfere with such assays. Anti-8EPGF2 did not cross-react with $9\beta$-$11\alpha$-$PGF_{2\alpha}$, $PGF_{2\alpha}$, 6-keto-$PGF_{1\alpha}$, 8-epi-PGF1$\alpha$ (5,6-dihydro-8-iso-$PGF_{2\alpha}$, 13,14-dihydro-$PGF_{1\alpha}$, 13-14-dihydro-15-keto-$PGF_{1\alpha}$, $PGF_{1\beta}$, 8-epi-$PGF_{1\beta}$, $11\beta$-$PGF_{1\beta}$, prostaglandin $E_2$, $PGD_2$ or arachidonic acid. There was a slight cross-reaction with $9\alpha$-$11\beta$-$PGF_2$ and 13-14-dihydro-15-keto-$PGF_{2\alpha}$ (4.1% and 3% respectively). This result showed that anti-8EPGF2 IgG does not recognize eicosanoids when (a) stereochemistry of the bond between C7 and C8 is inverse (e.g. $PGF_{2\alpha}$), or (b) side chains of C9 is oxygenated (oxygenated side chain is planar to a ring structure of PG) or in a $\beta$ position.

The specificity of the antibody developed against 8EPGF2 was further investigated utilizing immunoaffinity chromatography. Immunoaffinity columns were prepared and increasing amounts of synthetic 8EPGF2 were applied to the immunoaffinity column (100 $\mu$l of resin cross-linked with anti-8EPGF2 IgG). Levels of unbound 8EPGF2 were measured by ELISA. The unbound 8EPGF2 levels after applying up to 10 ng of 8EPGF2 were lower than 2%. This result shows that, under this experimental condition, higher than 98% of applied 8EPGF2 was bound to the antibody cross-linked to resin.

Figure 4A:
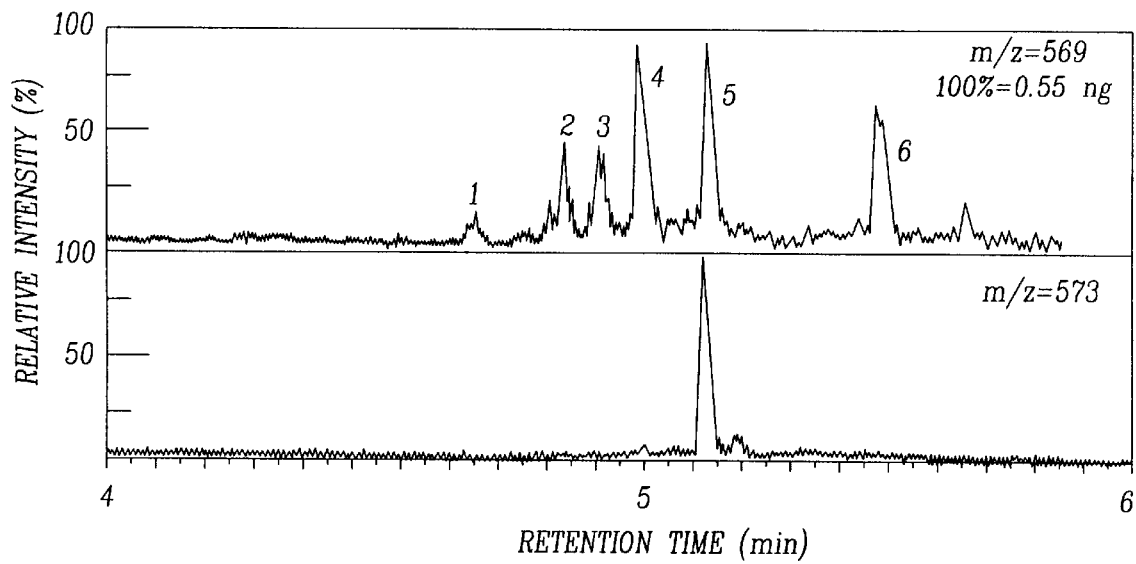
FIG. 4A–B are selected ion current chromatograms obtained from urine specimens after immunoaffinity column purification, showing the specificity of anti-8-epi-prostaglandin $F_{2\alpha}$ (8EPGF2) IgG among 8EPGF2 isomers wherein urine specimens were prepared using the standard solid phase extraction protocol (two column method) without (A) or with (B) pretreatment of urine samples by immunoaffinity chromatography. Quantitation of peaks with m/z=569 was based on a peak area of the known quantity (1.5 ng) of the internal control peak. The 8EPGF2 levels calculated from the GC elution profiles in A and Panel B were 2.24 and 1.82 ng, respectively.
Figure 4B:
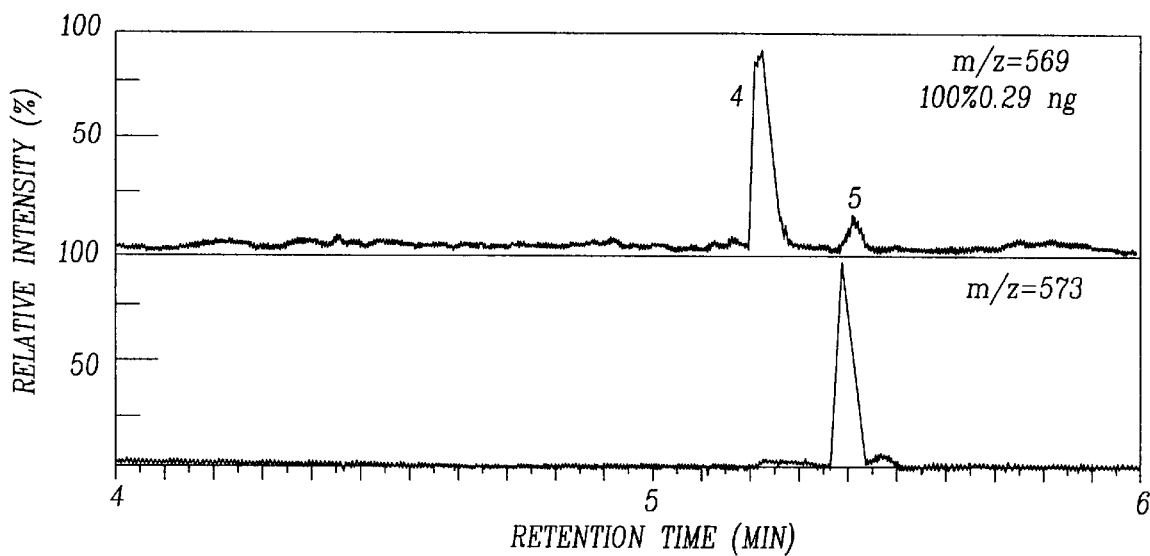

Urine samples were applied to immunoaffinity columns, which were then eluted with acetonitrile:water (1:3), followed by acetone:water (90:10). The eluates were then processed and analyzed using the standard GC/MS protocol as described herein above. The GC/MS profile of a urine specimen prepared using the standard solid phase extraction protocol (two column method) without an immunoaffinity purification step showed 6 peaks at m/z=569 (FIG. 4A). The GC/MS profile of an aliquot of the same urine specimen that was subjected to anti-8EPGF2 immunoaffinity chromatography prior to standard solid phase extraction showed a primary 8EPGF2 peak (m/z=569) (FIG. 4B). A small peak of $PGF_{2\alpha}$ (Peak V) eluted right after 8EPGF2 on GC (FIG. 4). $PGF_{2\alpha}$ has a slightly longer retention time than the $[^2H_4]$-$PGF_{2\alpha}$ (the internal control) shown in the bottom chromatograms of FIG. 4A and 4B, because protium runs faster than deuterium on GC [Wendelborn et al, 1990]. The six peaks with m/z=569 are numbered by the order of elution and the elution time of each peak was divided by the elution time of internal standard, $[^2H_4]$-$PGF_{2\alpha}$, obtained at m/z=573 to calculate relative elution time of each peak. The relative elution times of Peak I to VI were 0.91, 0.95, 0.96, 0.97, 1.00, and 1.07. The relative elution time for 8EPGF2 was 0.97 (FIG. 4). The identity of Peak I, II, III, and VI is not known. Ratio of Peak IV area to $[^2H_4]$-$PGF_{2\alpha}$ area GC profile obtained without immunoaffinity chromatography of urine specimen was 1.5:1, whereas ratio of those with immunoaffinity column chromatography was 1.2:1. The recovery rate of 8EPGF2 after immunoaffinity column chromatography calculated from the GC elution profiles was 80%, which is close to the values (85%) obtained using $[^3H]$-8EPGF2.

EXAMPLE 2

ESTERIFIED FORMS OF ISOPROSTANES

Recognition of Esterified 8EPGF2 by anti-8EPGF2 IgG

Anti-8EPGF2 IgG failed to cross-react with intact lipoproteins because fatty acid moieties of lipids were not exposed on the surface of lipoproteins (Table 2). However, anti-8EPGF2 IgG recognized free or esterified 8EPGF2 released from lipid bilayers and lumens of lipoproteins when the lipoproteins were digested with a lipase purified from yeast, *Candida cylindraccae*, or extracted with methanol:chloroform (2:1) solution (Table 2). The 8EPGF2 levels in the lipoproteins were measured by ELISA after treatment of low-density lipoproteins (LDL), oxidized LDL, and high-density lipoprotein (HDL) with lipase, extraction of these with methanol:chloroform (2:1) solution followed by treatment with lipase. The 8EPGF2 levels of oxidized LDL were >10-fold higher than those of LDL, and 8EPGF2 levels of LDL were ~3-fold higher than that of HDL (Table 2).

The levels of immunoreactive 8EPGF2 in extracts obtained from oxidized LDL was 341.5 pg/mg (Table 2). However, when the extracts were cleaved with lipase, the levels of immunoreactive 8EPGF2 increased to 795.7 pg/mg. This results demonstrate lower efficiency of the antibodies for binding esterified 8EPGF2 compared with binding free 8EPGF2. Binding properties of the antibodies for esterified 8EPGF2 has been characterized by obtaining a ratio of free and esterified forms in the extracts (1:6.0) by GC/MS followed by calculation of efficiency in immunoreactivity of esterified forms (Table 4). Contribution of immunoreactivity by esterified form before cleavage was 227.7 pg/mg oxidized LDL. The value increased to 681.9 (795.7–113.8) pg/mg of oxidized LDL after lipase cleavage. The percent efficiency in immunoreactivity of esterified form was ~33.4%.

Further Oxidation or Degradation of 8EPGF2 In Vitro

Levels of 8EPGF2 rapidly increased after 1 to 2 hours incubation of LDL with $Cu^{2+}$, whereas those of LDL incubated without $Cu^{2+}$ stayed at basal levels (Table 3).

EXAMPLE 3

CONJUGATED FORMS

Existence of a Conjugated form of 8EPGF2 in Urine Specimens

The levels of immunoreactive 8EPGF2 in normal urine specimens were higher than the values obtained by using GC/MS. This implies that the antibody against 8EPGF2 cross-reacts with free 8EPGF2 as well as other 8EPGF2 related molecules in urine specimen.

The recovery of 8EPGF2 was determined using a urine sample spiked with 8EPGF2 (1 ng) [after extraction of 8EPGF2 in urine with C18 column chromatography followed by silica gel chromatography (two column method)] was measured by ELISA. The levels of 8EPGF2 in an eluate of the urine sample were 2.2 ng, which is comparable to the expected 2.13 ng value. This result showed that 100% of free 8EPGF2 in urine (natural or spiked synthetic 8EPGF2 in a free form) was recovered. The high recovery rate of free 8EPGF2 following the solid phase extractions was confirmed using [$^3$H]-labeled 8EPGF2. Recovery rates of [$^3$H]-labeled 8EPGF2 spiked in urine specimens were 95% (Table 1).

Figure 5A:
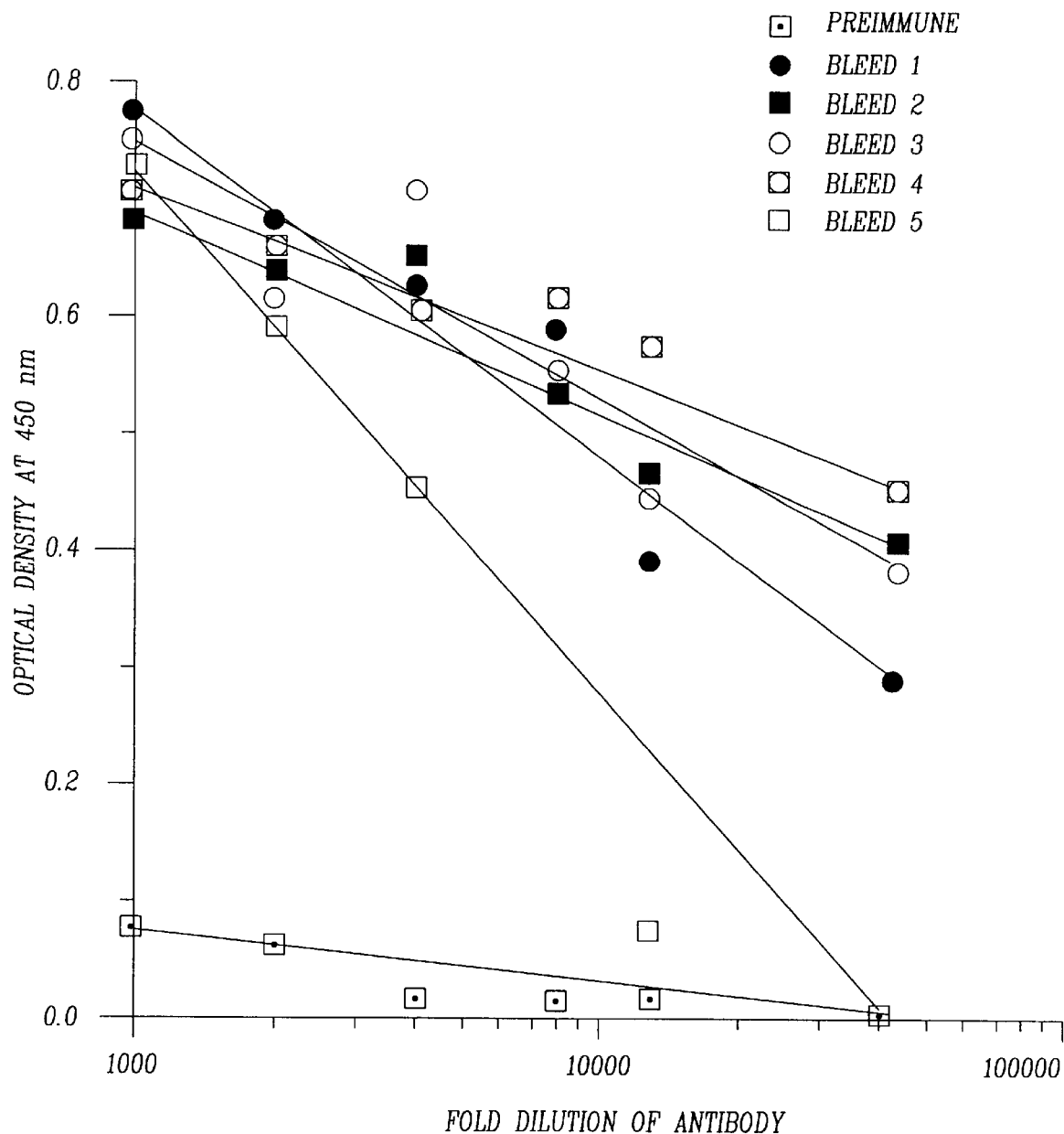
FIG. 5A–B are graphs showing cross-reactivity of anti-8-epi-prostaglandin $F_{2\alpha}$ (8EPGF2) IgG with protein conjugated 8EPGF2. Cross-reactivity of antibody against 8EPGF2 with 8EPGF2 conjugated to ovalbumin (A) or ovalbumin alone as a negative control (B) was determined by ELISA. One µg of 8EPGF2 conjugated ovalbumin or albumin per well was coated on plates. Non-specific binding to plates coated with ovalbumin was low (B).
Figure 5B:
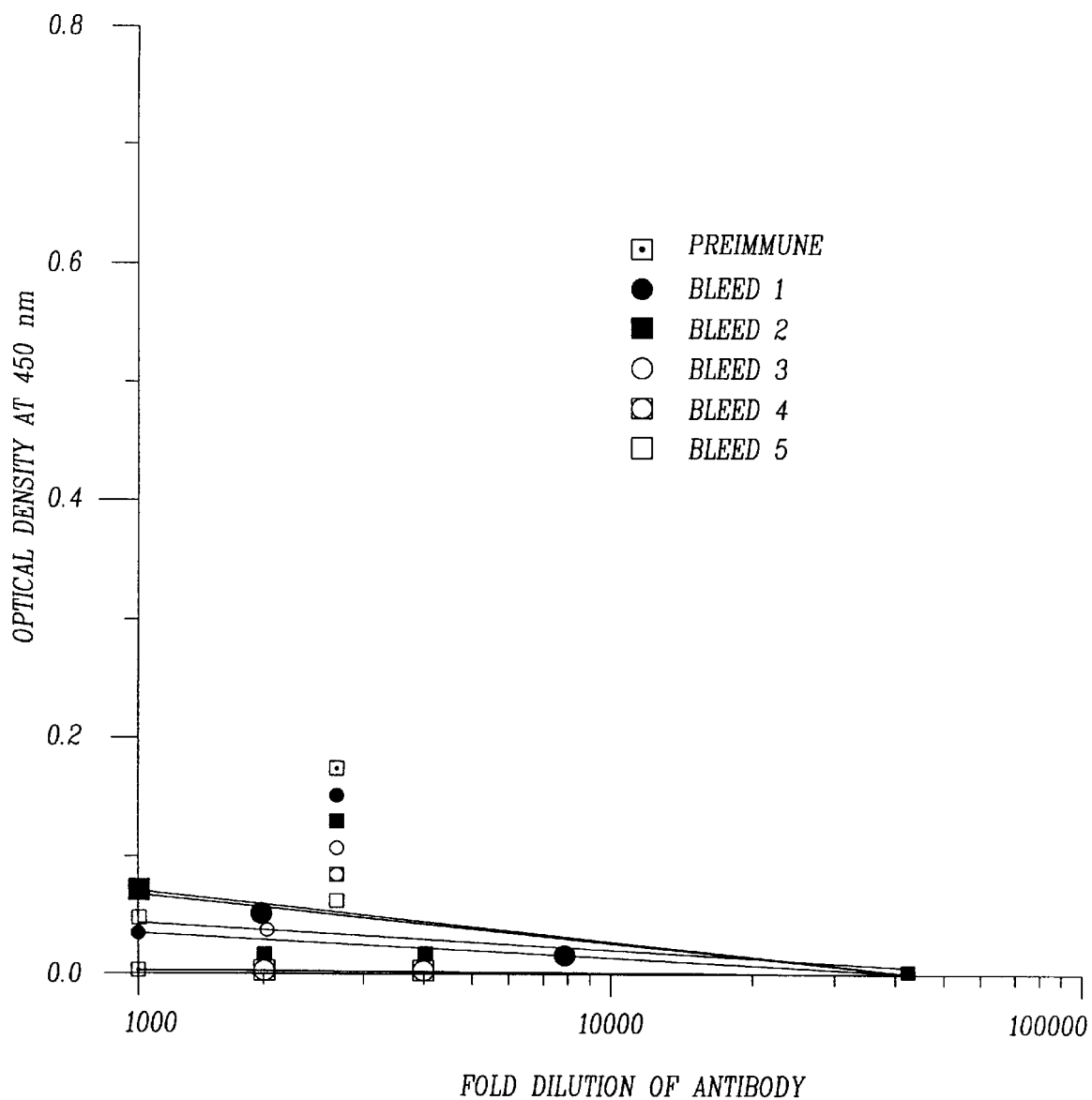

Contrary to the high, almost 100%, recovery of the free 8EPGF2, recovery rates of immunoreactive 8EPGF2 in urine specimens following C18 solid phase extraction, or C18 solid phase extraction followed by silica solid phase extraction were 58% and 22%, respectively (Table 1). Recovery of 8EPGF2 in urine specimens following a liquid phase extraction with ethyl acetate mixed with citric acid [5:1 (v/w)] was also low (22%). These results suggest that GC/MS procedure, which includes treatment of urine specimens with the two column method, measures only free 8EPGF2 in urine and the discrepancy in recovery rates of 8EPGF2 with different extraction methods was a result of the existence of isoprostane metabolites with physical properties different from free 8EPGF2 but which retain immunoreactivity with anti-8EPGF2. Immunogens were produced by cross-linking 8EPGF2 to BSA through the carboxyl group of 8EPGF2. As expected, the antibodies recognized 8EPGF2 cross-linked to ovalbumin through the carboxyl groups (FIG. 5). These results suggest that the antibodies recognize 8EPGF2 conjugated to proteins via the carboxyl group of the molecule.

Free and Conjugated 8EPGF2 Levels in Urine Specimens of Heavy Smokers

Figure 6:
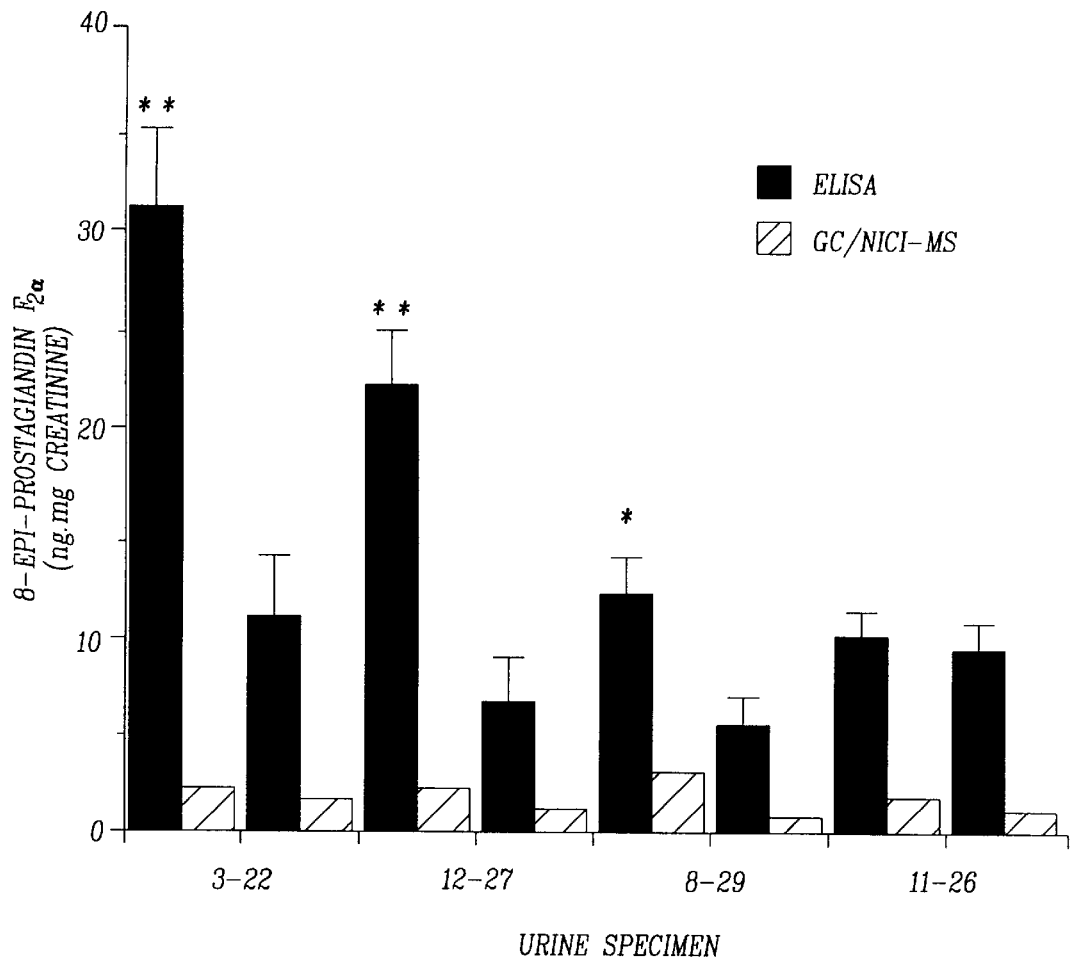
FIG. 6 is a bar graph showing the effects of smoking on urinary 8EPGFF2 levels. The urine samples were measured by ELISA (n=6, 3 repetitions) without pretreatment or by GC/NICI-MS after urine samples were purified by the two column method. Urine specimens from smokers (3, 8, 11, 12) and age and sex matched controls (22, 29, 26, 27 respectively). * denotes significance at p>0.05 different from the value obtained from its corresponding non-smoker urine. **denotes significance at the P>0.01 level.

The levels of 8EPGF2 in urine specimens obtained from heavy smokers by ELISA and GC/NICI-MS (FIG. 6) was measured. The 8EPGF2 levels in urine samples were measured by ELISA without pretreatment or GC/NICI-MS after purification of urine samples by the two column method. Urine specimens obtained from smokers were specimens Number 3, 8, 11 and 12, and their corresponding age- and sex-matched non-smokers were specimens number 22, 29, 26 and 27, respectively. The levels of 8EPGF2 measured by ELISA in urine specimens obtained from each smoker and non-smoker pair are shown in order of decreasing values of smokers in FIG. 6. Corresponding values obtained by GC/NICI-MS are also shown. The 8EPGF2 levels in smokers urine specimens were ~1.5 to 3-fold higher than those of non-smokers as obtained by both ELISA and GC/NICI-MS. The levels of 8EPGF2 measured by ELISA in urine specimens were ~4- to 15-fold higher than the levels of these measured by GC/NICI-MS. Levels of 8EPGF2 obtained by GC/NICI-MS after purification of urine using a two column method is a measurement of free 8EPGF2 whereas levels of 8EPGF2 obtained by ELISA without purification of urine is a measurement of both free 8EPGF2 and isoprostane metabolites with physical properties different from free 8EPGF2 but which retain immunoreactivity with anti-8EPGF2. These results demonstrate that conjugated 8EPGF2 molecules were lost during extraction or purification of urine by the two column method.

EXAMPLE 4

IDENTIFICATION OF GLUCURONIDATED FORM

Increase of 8EPGF2 Levels in Urine Specimen after Hydrolysis with β-Glucuronidase Human urine specimen was digested with β-glucuronidase and the immunoreactive 8EPGF2 levels of the digested urine specimen was compared with that of predigestion. Immunoreactive 8EPGF2/mg was about 20 ng of creatinine increased after the digestion (Tables 5 and 6). This result showed that at least ~29% of 8EPGF2 is excreted in urine as a glucuronidated form. The fraction of immunoreactive 8EPGF2 in urine dramatically increased after hydrolysis of urine specimen with β-glucuronidase.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

Concentrations of 8-epi-prostaglandin $F_{2\alpha}$ (8EPGF2) if urine determination with or without prior extraction.
Levels of 8EPGF2 in urine with or without prior extraction of 8EPGF2 were measured by ELISA using anti-8EPGF2 IgG. Recovery of [$^3$H]-labeled 8EPGF2 spiked to the urine was also measured by ELISA. Urine samples were acidified to pH 3.0 with HCl before they were subjected to C18 solid phase extraction (one column method), C18 solid phase extraction followed by silica solid phase extraction (two column method), or liquid phase extraction.

| | Levels of 8-epi-PGF2α | | | |
|---|---|---|---|---|
| | EIA | | Recovery of Spiked [$^3$H] 8-epi-PGF2α | |
| Treatment | ng/ml | % | DPM | % |
| None | 18.6 ± 2.4 | 100 | 13580 | 100 |
| C18 Solid Phase Extraction | 10.7 ± 2.5 | 57.6 ± 13.5 | 12954 | 95.4 |
| C18 Solid Phase Extraction followed by Silica Solid Phase Extraction[1] | 4.1 ± 0.3 | 21.8 ± 1.9 | 12921 | 95.1 |
| Liquid Phase Extraction with Ethyl Acetate Mixed with Citric Acid | 4.1 ± 0.6 | 21.9 ± 3.5 | NT | NT |

[NT]Not Tested
[1]Multiple extraction protocol used for GC/MS analysis without thin layer chromatography

TABLE 2

Levels of 8EPGF2 In low density lipoprotein (LDL), oxidized LDL, and high density lipoprotein (HDL).

| | 8-epi-PGF2α (pg/mg LDL or HDL) | | |
|---|---|---|---|
| Treatment | LDL | Oxidized LDL | HDL |
| None | 0 | 0 | 0 |
| Lipase Cleavage | 107.6 ± 29.8 | 1,082.3 ± 55.9***** | 29.4 ± 11.9* |
| Extraction | 24.0 ± 8.9 | 341.5 ± 145.5* | NT |

TABLE 2-continued

Levels of 8EPGF2 In low density lipoprotein
(LDL), oxidized LDL, and high density
lipoprotein (HDL).

| | 8-epi-PGF2α (pg/mg LDL or HDL) | | |
|---|---|---|---|
| Treatment | LDL | Oxidized LDL | HDL |
| Extraction Followed by Lipase Cleavage | 16.0 ± 5.1 | 795.7 ± 134.9***** | NT |

NTNot Tested
*Significantly (P < .05) different from LDL.
*****Significantly (P < .00001) different from LDL.

TABLE 3

Increase of 8EPGF2 levels in LDL after In vitro Oxidation.
LDL was obtained from PerImmune, Inc. (Rockville, MD) and antioxidants and low molecular weight contaminants in LDL were removed by passing through Sephadex G25M PD-10 gel filtration columns (Pharmacia Co., Piscataway, NJ) according to manufacturer's instructions prior to incubation of LDL (100 mg/ml) with 5 µM $CuSO_4$ at 37° C. Aliquots were removed at intervals and spun in microtubes. Supernatants were removed and digested with yeast lipase for 2 hours before quantitation of 8EPGF2 levels by ELISA. Minor oxidation of LDL observed during lipase digestion was subtracted from final 8EPGF2 levels.

| Incubation Time | 8-epi-PGF2α Levels in LDL (ng/mg LDL) | |
|---|---|---|
| (hr) | No Addition | $Cu^{2+}$ Addition |
| 0 | 0.039 ± 0.030 | 0.039 ± 0.030 |
| 1 | 0.010 ± 0.009 | 35.692 ± 8.416*** |
| 2 | 0 | 31.892 ± 11.333*** |

***Significantly (P < .001) different from the value obtained without incubation at 37° C.

TABLE 4

Immunoreactivity of antibodies against 8EPGF2 for esterified EPGF2

| | 8-epi-PGF2α (pg/mg oxidized LDL) |
|---|---|
| Total | 795.7 |
| Free Form | 113.8 |
| Esterified Form | 681.9 |
| Immunoreactivity of Esterified Form (Efficiency) | 227.7 (0.334) |

TABLE 5

Increase of Immunoreactive 8EPGF2 levels after hydrolysis with β-glucuronidase.

| | 8EPGF2 Levels of Urine Specimens | | | |
|---|---|---|---|---|
| | 1 | | 2 | |
| Treatment | ng/mg of creatinine | % of control | ng/mg of creatinine | % of control |
| None | 50.48 ± 0.02 | 100 | 33.42 ± 0.02 | 100 |
| Hydrolysis | 69.66 ± 0.02 | 138.0 ± 0.04 | 41.16 ± 0.03 | 123.2 ± 0.09 |

TABLE 6

Immunoassay of free and glucuronide conjugated urinary 8EPGF2

| | Treatment: 8EPG2 (ng/mg creatinine) | | Ratio | Difference |
|---|---|---|---|---|
| Subject | None | β-Gluc | (+/−β-gluc) | (=conjugated) |
| Experiment #1 | | | | |
| Male smoker | 9953 | 31230 | 3.14 | 21277 |
| Male non-smoker | 5020 | 12857 | 2.56 | 7837 |
| Female smoker | 9953 | 33654 | 3.38 | 23701 |
| Experiment #2 | | | | |
| Female Non-smoker | 8192 | 12497 | 1.52 | 4305 |
| Female Non-smoker (V) | 8389 | 8332 | 0.99 | −57 |
| Female smoker | 2797 | 5838 | 2.08 | 3041 |
| Female smoker(V) | 14705 | 17083 | 1.16 | 2378 |

Note: in the first experiment urine samples were analyzed by ELISA±glucuronidase treatment without prior solid extraction. In the second experiment samples were filtered prior to analysis. V indicates a second urine sample obtained from each individual following a seven day course of antioxidant vitamin supplementation (1000 mg/day Vitamin C+800 mg/day Vitamin E).

REFERENCES

Awad, et al (1993) J. Biol. Chem. 268:4161–4169.
Awad, et al (1994) J. Nutr. 124:810–816.
Fukunaga, (1993) Am. J. Physiol. 264:C1619–C1624.
Halliwell et al (1987) The measurement of free radical reactions in humans: Some thoughts for future experimentation. FEBS Letters 213:9–14.
Jansen, et al (1991) New developments in glucuronidation research. Hepatology 15:532–544.
Levine and VanVunakis, (1972) Biochem. Biophys. Res. Comm. 47:888–896.
Lynch, et al (1994) J. Clin. Invest. 93:998–1004.
Morrow, et al, (1990a) Anal. Biochem. 184:1–10.
Morrow, et al, (1990b) Proc. Natl. Acad. Sci. U.S.A. 97:9383–8387.
Morrow and Roberts, (1991). Free Rad Biol. Med. 10:195–200.
Morrow, et al (1994) Int. J. Biochim. Biophys. 1210:244–248.
Morrow, et al (1995) N. Engl. J. Med. 332:1198–1203.
Morrow and Roberts (1997) The Isoprostanes: Unique bioactive products of lipid peroxidation. Prog. Lipid Res 36:1–21.
Pace-Asciak and Wolfe, (1971) J. Chromatogr, 56, 129–133.
Proudfoot, et al (1995) Biochem. Biophys. Res. Comm. 206:455–461.
Rich and Singh (1979) The Peptides 1:241–261.
Roberts (1987) Comparative metabolism and fate of the eicosanoids. In CRC Handbook of Eicosanoids: Prostaglandins and Related Lipids (Willis, ed., CRC Press, Boca Raton, Fla.) pp 233–244.
Rosenkranz et al (1980a) Identification of the major metabolite of prostacyclin and 6-keto-prostaglandin Fla in man. Biochi. Biophys. Acta 619:207–213.
Rosenkranz et al (1980b) Metabolism of prostacyclin and 6-keto-prostaglandin Fla in man. J. Biol. Chem. 255:10194–10198.
Takahashi, et al (1992) J. Clin. Invest. 90:136–141.

Wendelborn et al, (1990) in Methods in Enzymol. 187:51–62.

Huston et al, 1991 "Protein engineering of single-chain Fv analogs and fusion proteins" in Methods in Enzymology (J. J. Langone, ed.; Academic Press, New York, N.Y.) 203:46–88.

Johnson and Bird, 1991 "Construction of single-chain Fvb derivatives of monoclonal antibodies and their production in *Escherichia coli* in Methods in Enzymology (J. J. Langone, ed.; Academic Press, New York, N.Y.) 203:88–99.

Mernaugh and Mernaugh, 1995 "An overview of phage-displayed recombinant antibodies" in Molecular Methods In Plant Pathology (R. P. Singh and U. S. Singh, eds.; CRC Press Inc., Boca Raton, Fla.) pp. 359–365.

What is claimed is:

1. A method to assess oxidative stress in vivo by measuring the amount of free, esterified and glucuronidated forms of isoprostanes in a biological sample containing the isoprostanes and determining a measured amount of total isoprostanes present in the sample, and comparing the measured amount with a healthy control sample and thereby assessing the oxidative stress through said comparison wherein the total amount of isoprostanes increases in the sample isolated from an organism undergoing oxidative stress in vivo compared to the control.

2. The method of claim 1 wherein the biological sample is selected from the group consisting of plasma, urine, cerebrospinal fluid, bile and joint fluid.

3. The method of claim 2 wherein the biological sample is urine.

4. The method of claim 1 wherein said measuring step is an immunoassay.

5. The method of claim 4 wherein the immunoassay is performed following hydrolyzation of the sample.

6. The method of claim 1 wherein said measuring step for glucuronidated forms of isoprostanes includes the steps of separating utilizing column chromatography the free form from glucuronidated forms resulting in a free fraction and glucuronidated fraction, hydrolyzing the glucuronidated fraction to release the free form and measuring the released free form as a means of determining the amount of glucuronidated isoprostane.

7. A method to assess oxidative stress in vivo by measuring the amount of glucuronidated isoprostanes in a biological sample containing the isoprostanes and determining the amount of glucuronidated isoprostane present in the sample, and comparing the measured amount with a control sample and thereby assessing the oxidative stress through said comparison wherein the total amount of glucuronidated isoprostanes increases in the sample from an organism undergoing oxidative stress compared to the control.

8. The method of claim 7 wherein said measuring step is an immunoassay.

9. The method of claim 6 wherein the biological sample is selected from the group consisting of plasma, urine, cerebrospinal fluid, bile and joint fluid.

10. The method of claim 9 wherein the biological sample is urine.

* * * * *